US007112714B2

(12) United States Patent
Leber

(10) Patent No.: US 7,112,714 B2
(45) Date of Patent: Sep. 26, 2006

(54) TOPICAL WOUND DRESSING AND METHOD OF MAKING SAME

(76) Inventor: Claudia K. Leber, 8922 N. 114th Ln., Peoria, AZ (US) 85345

( * ) Notice: Subject to any disclaimer, the term of this patent is extended or adjusted under 35 U.S.C. 154(b) by 0 days.

(21) Appl. No.: 10/979,457

(22) Filed: Nov. 1, 2004

(65) Prior Publication Data

US 2006/0094996 A1    May 4, 2006

(51) Int. Cl.
*A61F 13/00* (2006.01)
(52) U.S. Cl. .......................... 602/48; 424/449; 424/402
(58) Field of Classification Search ............ 602/41–43, 602/48; 424/443–449, 402; 604/304–308
See application file for complete search history.

(56) References Cited

U.S. PATENT DOCUMENTS 4,884,563 A * 12/1989 Sessions ...................... 602/57

FOREIGN PATENT DOCUMENTS

JP        2184626     *  7/1990

* cited by examiner

Primary Examiner—Henry Bennett
Assistant Examiner—Camtu Nguyen
(74) Attorney, Agent, or Firm—Gregory J. Nelson

(57) ABSTRACT

A topical dressing and method of making same wherein a gauze pad is impregnated with tannin extract derived from Black Pekoe tea.

5 Claims, 2 Drawing Sheets

```
┌─────────────────────────┐
│ ADD BLACK PEKOE         │
│ TEA LEAVES TO WATER     │
└─────────────────────────┘
            │
┌─────────────────────────┐
│ MAINTAIN TEMP. OF       │
│ MIXTURE AT 90°C         │
│ FOR 4 HOURS             │
└─────────────────────────┘
            │
┌─────────────────────────┐
│ REMOVE SOLIDS           │
│ FROM MIXTURE            │
└─────────────────────────┘
            │
┌─────────────────────────┐
│ IMMERSE GAUZE           │
│ IN AQUEOUS SOLUTION     │
│ FOR 12 HOURS            │
└─────────────────────────┘
            │
┌─────────────────────────┐
│ STERILIZE AND DRY       │
│ IMPREGNATED GAUZE       │
└─────────────────────────┘
            │
┌─────────────────────────┐
│ PLACE GAUZE             │
│ IN STERILE PACKAGE      │
└─────────────────────────┘
```

TOPICAL WOUND DRESSING AND METHOD OF MAKING SAME

BACKGROUND OF THE INVENTION

This invention relates to a topical dressing for the treatment of wounds or surgical incisions. In particular, the invention is directed to a dressing impregnated with a mixture of tannins which will stimulate the blood clotting process. The dressing is prepared in a manner which renders it usable in sterile environments.

A wide spread use of aspirin therapy throughout the general population to reduce the clotting characteristics of blood along with the increased prescribing of anticoagulant drugs, such as warfarin sulfate and heparin, have created difficulties for medical practitioners in treating patients taking anticoagulant drugs. In order for doctors and dentists to engage in procedures which are likely to generate blood flow from a wound created in the course of the procedure, the patient is often told to cease taking the medication for a period of several days and perhaps a week before returning to have the procedure performed. For a patient with a pain-inducing tooth to have to endure the accompanying pain for an extended period before an extraction can be performed, the wait is more than just inconvenient.

Many persons are placed on a regimen of anticoagulant drugs because of major health problems wherein the possibility of vascular clotting has serious implications. Patients in these categories are advised not to discontinue their anticoagulant medication in view of the potential adverse consequences. As a result, extraordinary procedures are often required to bring about a cessation of blood flow from even minor procedures. These patients can be made subject to additional risks even from routine procedures which the general population regards as relatively minor procedures.

Accordingly, the present invention is directed to a dressing for a wound which facilitates and hastens the cessation of blood flow therefrom. The dressing is a sterile impregnated gauze wherein the impregnant is a plant-based astringent that exhibits antibacterial properties and causes blood coagulation which aids in closure of the wound. The impregnant is a solution of black teas from the Pekoe plant and sterile water. The gauze dressing is sufficiently durable to allow pressure to be applied thereto further aiding in the closure of the wound.

SUMMARY OF THE INVENTION

The invention relates to impregnated gauze pads for use in accelerating a reduction of blood flow from a wound. The impregnant utilized is a plant-based astringent containing a mixture of tannins, also known as polyphenols, that are found in Black Pekoe tea. The source of impregnant is the extract of the Black Pekoe tea leaves. Heating the leaves in water leaches a tannin-rich extract from the leaves which enters into solution with the water. The leaching takes place over a period of several hours at a temperature of about 90 degrees C. These tannins or polyphenols are of a very large molecular weight that binds proteins this promoting clot formation.

The impregnation of the gauze can take place by its immersion in the aqueous solution of the tannin extract, followed by drying and placement in a sterile container. Since the impregnated gauze is to be placed in contact with an open wound, the components and the manufacturing environment should be sterile. In the case of pads, the drying step is followed by sterilization and the impregnated pads can be packaged impregnated with the tannin extract and ready to be placed on a wound.

In use, the open wound is treated by placing the gauze dressing on the wound in an overlying position. Modest pressure is applied to promote contact with the subject being treated. When the subject invention is used in dental applications, e.g. following an extraction of a tooth, the gauze dressing in the form of a pad is held in position by jaw pressure conveyed by an opposing tooth. This is strictly a topical application, thus not interfering with systemic problems or encouraging clotting in areas other than the wound.

The tannin extract possesses an astringent characteristic which acts as an antibiotic and coagulant thereby assisting the subject in reducing blood flow at a wound site. The subject invention is not limited to use by medical professionals and can be applied to scrapes and other types of surface lesions as well as wounds.

Further features and advantages will become more readily apparent from the following detailed description of the invention when viewed in conjunction with the accompanying drawings.

DESCRIPTION OF THE PREFERRED EMBODIMENT

The present invention is directed to a wound dressing and the method of making same. The dressing includes a cotton gauze carrier impregnated with the tannin extract obtained from Black Pekoe tea. The application of the impregnated gauze to a wound such as that resulting from an extraction of a tooth has been found to promote both blood clotting and wound closure. In tests on the same patient undergoing multiple extractions, the benefits of the application of the gauze prepared in accordance with the present invention were observed after one day and after seven days following the extraction. Furthermore, patients reported a taste benefit from use of the subject invention and attributed to the early cessation of blood flow from the wound.

Figure 1:
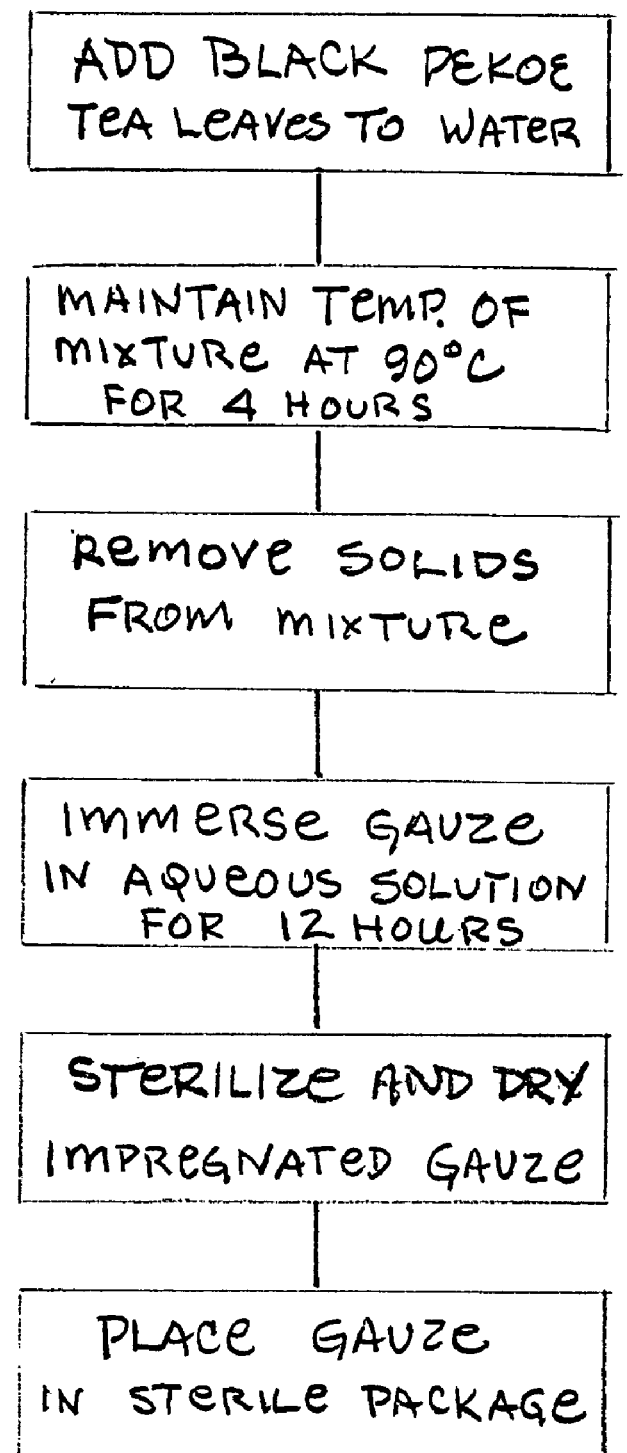
FIG. 1 is a block diagram showing the steps in the practice of the present invention.

The preparation of the impregnated gauze is shown in the block diagram of FIG. 1 as commencing with the addition of Black Pekoe tea leaves to distilled water. The term Black Pekoe refers to a black tea grown in Sri Lanka and India, made from the small leaves at the tips of the stem. The tea, either loose or confined, is added to water that is heated to about 90 degrees C. for a period of about four hours. The beneficial effects of the invention are not achieved if the water temperature is allowed to reach the boiling point. While not fully understood, it is believed that the tannin extract leached from the tea leaves is chemically altered if the mixture is brought to the boiling temperature and the beneficial results of the invention are not experienced.

The preferred quantity of tea leaves added to the solution is within the range of 17 to 21 grams of Black Pekoe tea leaves per eight ounces of water. The goal is to achieve a substantial saturation of the water with the tannin extract. The tannin extracts are the agent that colors the water and the darker the color the more closely the solution is to saturation. In practice, the tea solids remain in the water for about four hours. Next, the solids are removed from the mixture leaving the aqueous solution of tannin extracts dissolved in water.

Figure 2:
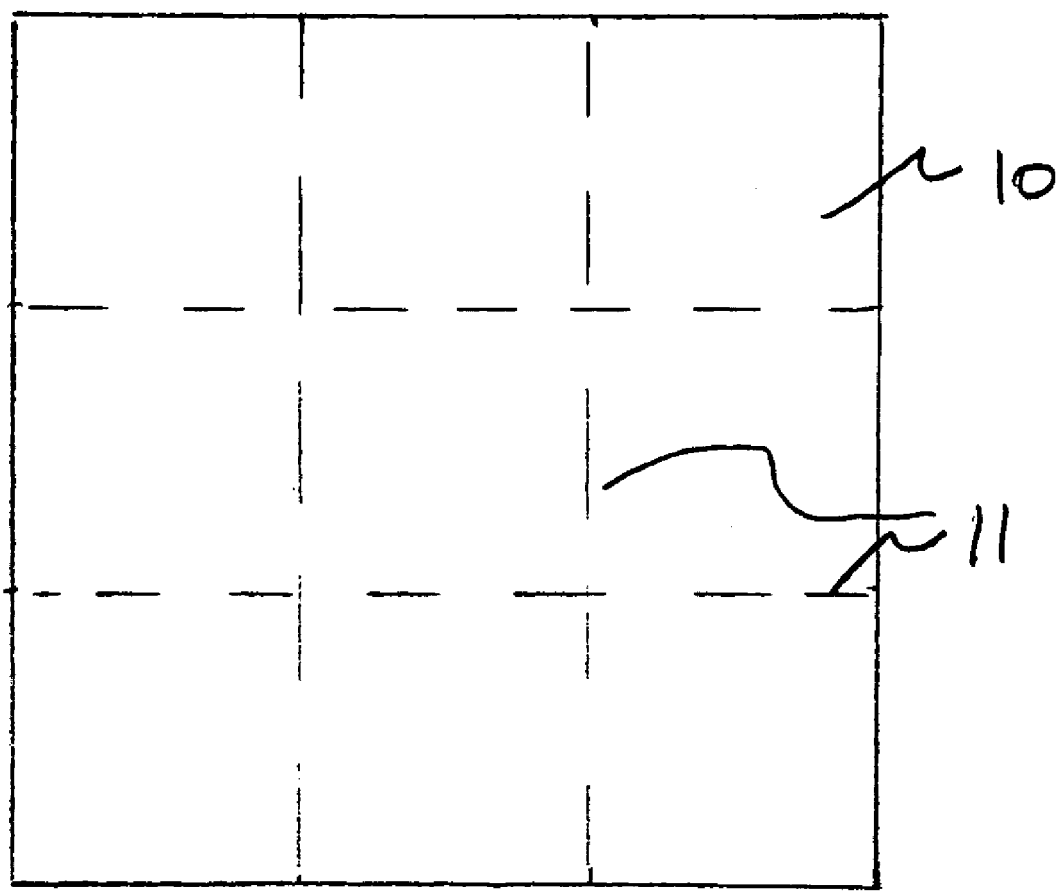
FIG. 2 is a plan view of an unfolded gauze pad.

The cotton gauze typically in the form of an opened pad 10 as shown in FIG. 2 is immersed in the solution. The dotted lines 11 of FIG. 2 represent the fold lines of a typical gauze pad such as the standard size 2×2 inch and 4×4 inch pads. The unfolded pads are immersed in the solution for about twelve hours.

Thereafter, the pads are sterilized and dried prior to placement in individual plastic pouches for later use. Sterilization can take place in an autoclave followed by use of the heat cycle of the sterilizer. Alternatively, sterilization can be attained by use of ultraviolet radiation.

As mentioned, comparative tests were conducted wherein dental patients having two extractions were provided with gauze impregnated in accordance with the invention at one wound site and with plain gauze at the other site. In addition, similar testing was conducted substituting other types of teas, e.g. Green tea, for the plain gauze in the case of patients having more than one extraction. The observations made in both series of tests showed faster blood clotting and accelerated healing of the wound, at one day and seven days, when the present invention was utilized as the wound dressing.

While the above description has referred to a particular embodiment of the invention, it is to be noted that modifications and variations may be made therein without departing from the scope of the invention.

What is claimed is:

1. A method of making a topical wound dressing which comprises the following steps:
   (a) adding Black Pekoe tea leaves to water;
   (b) maintaining the temperature of the mixture of tea leaves and water at about 90 degrees C. for a period sufficient to leach tannin extracts from said tea leaves and form a substantially saturated aqueous solution;
   (c) impregnating gauze with the aqueous solution;
   (d) drying the impregnated gauze; and
   (e) sterilizing the gauze, said impregnated gauze containing tannin extracts for dressing a wound.

2. The method in accordance with claim 1 wherein the period of maintaining the temperature of the mixture of tea leaves and water is about four hours.

3. The method in accordance with claim 2 wherein the step of impregnating the gauze includes immersing the gauze in the aqueous solution for a period of about twelve hours.

4. The method of claim 1 further comprising placing the sterilized gauze in a sterile package.

5. The method of claim 1 wherein said aqueous solution is a substantially saturated solution at 90 degrees C.

* * * * *